(12) United States Patent
Taylor et al.

(10) Patent No.: US 7,728,163 B2
(45) Date of Patent: Jun. 1, 2010

(54) MIXED FLUOROALKYL-ALKYL SURFACTANTS

(75) Inventors: Charles Kenneth Taylor, Thorofare, NJ (US); Michael Joseph Michalczyk, Wilmington, DE (US); Erick Jose Acosta, New Castle, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 104 days.

(21) Appl. No.: 11/890,395

(22) Filed: Aug. 6, 2007

(65) Prior Publication Data

US 2009/0042996 A1 Feb. 12, 2009

(51) Int. Cl.
*C07F 9/02* (2006.01)

(52) U.S. Cl. .................................... 558/204

(58) Field of Classification Search .................. 558/204
See application file for complete search history.

(56) References Cited

U.S. PATENT DOCUMENTS

| | | | |
|---|---|---|---|
| 3,128,272 A | 4/1964 | Wear et al. | |
| 3,719,698 A | 3/1973 | Tesoro et al. | |
| 4,296,034 A | 10/1981 | Bouvet et al. | |
| 5,502,251 A | 3/1996 | Pohmer et al. | |
| 5,608,116 A | 3/1997 | Halling et al. | |
| 6,060,626 A | 5/2000 | Fujii et al. | |
| 6,180,740 B1 | 1/2001 | Fitzgerald | |
| 6,451,717 B1 | 9/2002 | Fitzgerald et al. | |
| 6,506,806 B2 | 1/2003 | Taylor et al. | |
| 6,979,711 B2 | 12/2005 | Franchina | |
| 7,164,041 B1 | 1/2007 | Moore et al. | |
| 7,553,985 B2 * | 6/2009 | Shtarov et al. | 558/204 |
| 2004/0138080 A1 * | 7/2004 | DeSimone et al. | 510/285 |
| 2005/0107645 A1 | 5/2005 | Furukawa | |
| 2005/0197273 A1 | 9/2005 | Savu et al. | |
| 2006/0148671 A1 | 7/2006 | Dams et al. | |
| 2007/0049646 A1 | 3/2007 | Moore et al. | |

FOREIGN PATENT DOCUMENTS

| | | |
|---|---|---|
| EP | 0150942 A | 8/1985 |
| EP | 0164124 A | 12/1985 |
| EP | 1462434 A | 9/2004 |
| EP | 1496073 | 1/2005 |
| EP | 1505098 A | 2/2005 |
| FR | 2797764 A | 3/2001 |
| GB | 1372037 | 10/1974 |
| JP | 61291677 | 12/1986 |
| JP | 04080282 | 3/1992 |
| JP | 08208425 A | 8/1996 |
| JP | 2003131334 A | 5/2003 |
| JP | 2004161838 A | 6/2004 |
| JP | 2005054020 A | 3/2005 |
| WO | WO 02/26921 A1 | 4/2002 |
| WO | WO 2004067579 | 8/2004 |
| WO | WO 2005/113488 A1 | 1/2005 |
| WO | WO2008/070490 A | 6/2008 |

OTHER PUBLICATIONS

Shtarov et al, 2007, CAS: 146:464128.*
Yoshino et al., 2005, CAS: 144:56985.*
Stone et al., 2004, CAS: 140:255324.*
Keiper et al: "New Phosphate Fluorosurfactants for Carbon Dioxide" J. Am. Chem. Soc., vol. 124, No. 9, 2002, pp. 1834-1835, XP002499301 compound 2, figures 1-3, p. 1835, col. 2, line 1-line 8.
Keiper at al: "Self-Assembly of Phosphate Fluorosurfactants in Carbon Dioxide", Langmuir, 20(4), 1065-1072 CODEN: LANGD5; ISSN: 0743-7463, 2004, XP002499490 Abstract, compounds 5-13.
Selve Claude et al: "Synthesis of monodisperse perfluoroalkyl oxyethylene surfactants with methoxy capping: surfactants of high chemical inertness", Journal of The Chemical Society, Chemical Communications, Chemical Society. Letchworth, GB, Jan. 1, 1990, pp. 911-912, XP009112323.

(Continued)

*Primary Examiner*—Rei-tsang Shiao

(57) ABSTRACT

A surfactant of formula 1

$(R_f\text{-}A)_a\text{-}Q\text{-}([B]_k\text{—}R)_b$      Formula 1 wherein
a and b are each independently 1 or 2;
$R_f$ is a linear or branched perfluoroalkyl radical having from 2 to about 20 carbon atoms, optionally interrupted with at least one oxygen;
R is a $C_1$ to $C_{20}$ linear, branched or cyclic alkyl, or a $C_6$ to $C_{10}$ aryl;
B is —$(CH_2CHR^1O)_x$—,
k is 0 or 1, x is 1 to about 20,
A is —$(CH_2)_m[(CHR^1CH_2O)]_s$—$[(CH_2)_m(CH)_tCHOH(CH_2)_m]_e$—,
wherein
each m is independently 0 to 3, s is 0 to about 30, t is 0 or 1, and e is 0 or 1,
$R^1$ is H or $CH_3$,
Q is:
   —$OP(O)(O^-M^+)(O)$—,
   —O—,
   —S—$(CH_2)_m$—$C(O)$—O—,
   —$SO_2$—O—
   —$CH_2CH_2O$—$C(O)CH_2C(OH)(V)CH_2C(O)O$—;
   —$(CH_2CH_2O)_xCH_2CH(OH)$—$(CH_2CH_2O)_x$
   —$(CH_2)_m$—$Si[OSi(R^2)_3]_2$—, —$SO_2NR^2$—,
   —$(CH_2CH_2O)_zC(O)CH(SO_3^-M^+)CH_2C(O)(OCH_2CH_2)_z$—
wherein z is 1 to about 15, or
a bond when s is a positive integer,
V is —$C(O)OR^3$ and $R^3$ is H, $CH_3$ or $R_f$;
$R^2$ is $C_1$ to $C_4$ alkyl, and
$M^+$ is a Group 1 metal or an ammonium $(NH_xR^2_y)^+$ cation wherein x+y=4, and $R^2$ is $C_1$ to $C_4$ alkyl,
provided that when Q is —$OP(O)(O^-M^+)(O)$— or when Q is —$(CH_2CH_2O)_z$—$C(O)CH(SO_3^-M^+)CH_2C(O)(OCH_2CH_2)_z$—, then at least one of s or e is a positive integer.

9 Claims, No Drawings

OTHER PUBLICATIONS

Burger-Guerrisi et al: Research Article Temperature-induced phase transitions in fluorinated microemulsions: correlations between kinetics and structural observations:, J. Phys. Chem., vol. 92, No. 17, 1988, pp. 4974-4979, XP002520241, Abstract.

Tamura et al: "New Syntetic Method of Alky Perfluoroalkyl Ethers", SYNLETT, 2000, pp. 343-344, XP002520242.

Lehmler et al: "Synthesis and Structure of Environmentally Relevant Perfluorinated Sulfonamides", J. Fluorine Chem., vol. 128, Feb. 6, 2007, pp. 595-607, XP002520454, p. 595, col. 1, line 5.

Benefice-Malouet et al: J. Fluorine Chem., vol. 31, 1986, pp. 319-332, XP002520455.

Fujii et al: "A Convenient Catalytic Method for the Synthesis of Ethers from Alcohols and Carbonyl Compounds", Bull. Chem. Soc. Jpn., vol. 78, 2005, pp. 456-463, XP002520463.

Kumitake et al., Bilayer Membranes of Triple-Chain, Fluorocarbon Amphiphiles; J. Am. Chem. Soc. (1985), 107, 692-696.

Abenin et al., Synthèse de 3-[2F-alkyléthylamino]-1,2-époxypropanes et obtention de nouveaux tensioactifs mono ou bicaténaires à tête β-hydroxylée; J. of Fluorine Chemistry (1991), 55, 1-11. Abstract.

Guo et al., Hybrid Surfactants Containing Separate Hydrocarbon and Fluorocarbon Chains; Journal of Physical Chemistry (1992), 96(16), 6738-6742.

Guo et al., Exchange of Hybrid Surfactant Molecules Between Monomers and Micelles; Journal of Physical Chemistry (1992), 96(24), 10068-74.

Harrison et al., Water-in-Carbon Dioxide Microemulsions with a Fluorocarbon-Hydrocarbon Hybrid Surfactant; Langmuir (1994), 10, 3436-3541.

Myrtil et al., Double-tailed perfluoroalkyl telomeric surfactants derived from tris(hydroxymethyl)acrylamidomethane for medical applications; Macromol. Chem. Phys. (1994), 195, 1289-1304.

Yoshino et al., Surfactants having polyfluoroalkyl chains. II. Syntheses of anionic surfactants having two polyfluoroalkyl chains including a trifluoromethyl group at each tail and their flocculation-redispersion ability for dispersed magnetite particles in water; J. of Fluorine Chemistry (1995), 70, 187-191.

Yoshino et al., Syntheses of Hybrid Anionic Surfactants Containing Fluorocarbon and Hydrocarbon Chains; Langmuir (1995), 11(2), 466-469.

Ito et al., Micellar Solution Properties of Fluorocarbon-Hydrocarbon Hybrid Surfactants; Langmuir (1996), 12(24), 5768-5772.

Církva et al., Chemistry of [(perfluoroalkyl)methyl] oxiranes. Regioselectivity of ring opening with O-nucleophiles and the preparation of amphiphilic monomers; Journal of Fluorine Chemistry (1997) 84, 54-61.

Ito et al., Micelle Aggregating Condition of Fluorocarbon-Hydrocarbon Hybrid Surfactants in Aqueous Solution; Langmuir (1997), 13, 2935-2942.

Abe, Synthesis and applications of surfactants containing fluorine; Current Opinion in Colloid & Interface Science (1999) 4, 354-356.

Huc et al., Gemini surfactants: studying micellisation by $^1H$ and $^{19}F$ NMR spectroscopy; Chem Comm, Sep. 1, 1999.

Abe et al., Fluorocarbon Hybrid Surfactants Characterization of Admicelles and Its Solubilization; Ind. Eng. Chem. Res. (2000), 39, 2697-2703.

Oda et al., Aggregation Properties and Mixing Behavior of Hydrocarbon, Fluorocarbon, and Hybrid Hydrocarbon-Fluorocarbon Cationic Dimeric Surfactants; Langmuir (2000), 16, 9759-9769.

Saeki et al., Solubilization of Oily Compounds into Fluorocarbon-Hydrocarbon Hybrid Surfactant Admicelles Formed on Alumina Surfaces; Langmuir (2000), 16(26), 9991-9995.

Chevalier, New surfactants: new chemical functions and molecular architectures; Current Opinion in Colloid & Interface Science (2002), 7, 3-11.

Timperley et al., Fluorinated phosphorus compounds Part 6. The synthesis of bis(fluoroalkyl) phosphites and bis(fluoroalkyl) phosphorohalidates; J. of Fluorine Chemistry (2002), 113, 65-78.

Aydogan et al., Interfacial and Bulk Properties of the New Fluorocarbon-Hydrocarbon Hybrid Unsymmetrical Bolaform Surfactant; Langmuir (2003), 19(26), 10726-10731.

Kirmizialtin et al., New Surfactants design for $CO_2$ applications: Molecular dynamics simulations of fluorocarbon-hydrocarbon oligomers[a]; J. of Chemical Physics (2003), 119(9), 4953-4961.

Dupont et al., Hybrid Fluorocarbon-Hydrocarbon $CO_2$-philic Surfactants. 1. Synthesis and Properties of Aqueous Solutions; Langmuir (2004), 20, 9953-9959.

Genson et al., Interfacial Micellar Structures from Novel Amphiphilic Star Polymers; Langmuir (2004), 20, 9044-9052.

Sun et al., Solution Properties of Sulfate-type Fluoro-Hybrid Anionic Surfactants with a Benzene Ring in Their Molecules; Journal of Oleo Science (2004), 53(8), 371-376.

Inoue et al., Micelle Formation of Phosphate-type Hybrid Surfactants in Aqueous Solution; Journal of Oleo Science (2005), 54(2), 95-103.

Kondo et al., Hybrid fluorocarbon/hydrocarbon surfactants; Current Opinion in Colloid & Interface Science (2005) 10, 88-93.

Li et al., Thermodynamics of micellization of partially fluorinated cationic gemini surfactants and related single-chain surfactants in aqueous solution; Current Opinion in Colloid & Interface Science (2005), 287, 333-337.

Miyazawa et al., Synthesis of phosphate-type fluorocarbon-hydrocarbon hybrid surfactants and their adsorption onto calcium hydroxyapatite; Journal of Fluorine Chemistry (2005), 126(3), 301-306.

Miyazawa et al., Synthesis and Solution Properties of Sulfate-type Hybrid Surfactants with an Ethylene Spacer; Journal of Oleo Science (2005), 54(3), 167-178.

Miyazawa et al., Synthesis and Solution Properties of Nonionic Hybrid Surfactants with a Benzene Ring; Journal of Oleo Science (2005), 54(6), 361-368.

Nishida et al., Mixing behavior of fluorinated and hydrogenated gemini surfactants at the air-water interface; Journal of Colloid & Interface Science (2005), 284, 298-305.

Hoda et al., Langmuir monolayer properties of the fluorinated-hydrogenated hybrid amphiphiles with dipalmitoylphosphatidylcholine (DPPC); Colloids and Surfaces B: Biointerfaces (2006) 47, 165-175.

Yoshimura et al., Synthesis and surface-active properties of sulfobetaine-type zwitterionic gemini surfactants; Colloids and Surfaces A: Physiochem. Eng. Aspects (2006), 273, 208-212.

\* cited by examiner

MIXED FLUOROALKYL-ALKYL SURFACTANTS

FIELD OF THE INVENTION

The field of the invention is fluorochemical surfactants, in particular those containing a perfluoroalkyl group and a hydrocarbon group connected by a linking hydrophilic moiety.

BACKGROUND OF THE INVENTION

For surfactants and surface treatment agents having fluorochemical chains longer perfluoroalkyl chains contain a higher percentage of fluorine at a given concentration and provide better performance. However, fluorinated materials are more expensive. Reduction of the fluorine content with delivery of the same or higher performance is therefore desirable. Reducing the fluorine content would reduce the cost, but it is necessary to maintain product performance.

WO 2005/113488 described fluoroalkyl/alkyl (twin-tailed) surfactants of the structure $R_f\text{—}Z^1\text{—}CH[(O)_rSO_3M]\text{-}Z^2\text{—}R_h$, in which $R_f$ is a fluoroalkyl group that may have an ether bond; $R_h$ is an alkyl group; r is 1 or 0; when r is 0, $Z^1$ and $Z^2$ respectively are $\text{—}(CH_2)_{n1}\text{—}(X^1)_{p1}\text{—}$ and $\text{—}(X^2)_{q1}\text{—}$, and when r is 1, $Z^1$ and $Z^2$ respectively are $\text{—}(CH_2Y)_{p2}\text{—}CH_2\text{—}$ and $\text{—}(CH_2Y)_{q2}\text{—}$, wherein $X^1$ and $X^2$ are the same or different, and respectively are a divalent linking group; p1 is 0 or 1; q1 is 0 or 1; n1 is an integer of 1-10; Y is O, S, or NR (wherein R is H or a $C_1$-$C_4$ n-, iso-, sec-, or t-alkyl group); p2 and q2 respectively are 0 or 1 but were not all 0 at the same time; and M is H, alkali metal, half alkaline earth metal, or ammonium. These structures are disclosed as having surfactant activity in carbon dioxide, but no other media.

It is desirable to improve surfactant performance, in particular lowering surface tension in aqueous systems, and to increase the fluorine efficiency, i.e., boost the efficiency or performance of the surfactants so a lower proportion of the expensive fluorine component is required to achieve the same level of performance, or to have better performance using the same level of fluorine. Especially desirable would be surfactants with similar performance to current commercial products but having less fluorine present via shorter perfluoroalkyl groups. The present invention provides such surfactants.

SUMMARY OF THE INVENTION

The present invention comprises a surfactant of formula 1

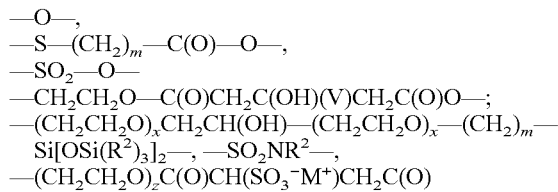   Formula 1 wherein
a and b are each independently 1 or 2;
$R_f$ is a linear or branched perfluoroalkyl radical having from 2 to about 20 carbon atoms, optionally interrupted with at least one oxygen;
R is a $C_1$ to $C_{20}$ linear, branched or cyclic alkyl, or a $C_6$ to $C_{10}$ aryl;
B is $\text{—}(CH_2CHR^1O)_x\text{—}$,
k is 0 or 1, x is 1 to about 20,
A is $\text{—}(CH_2)_m[(CHR^1CH_2O)]_s\text{—}[(CH_2)_m(CH)_t CHOH (CH_2)_m]_e\text{—}$, wherein
each m is independently 0 to 3, s is 0 to about 30, t is 0 or 1, and e is 0 or 1,
$R^1$ is H or $CH_3$,
Q is:
$\text{—}OP(O)(O^-M^+)(O)\text{—}$,
$\text{—}O\text{—}$,
$\text{—}S\text{—}(CH_2)_m\text{—}C(O)\text{—}O\text{—}$,
$\text{—}SO_2\text{—}O\text{—}$
$\text{—}CH_2CH_2O\text{—}C(O)CH_2C(OH)(V)CH_2C(O)O\text{—}$;
$\text{—}(CH_2CH_2O)_xCH_2CH(OH)\text{—}(CH_2CH_2O)_x\text{—}(CH_2)_m\text{—}Si[OSi(R^2)_3]_2\text{—}$, $\text{—}SO_2NR^2\text{—}$,
$\text{—}(CH_2CH_2O)_zC(O)CH(SO_3^-M^+)CH_2C(O)(OCH_2CH_2)_z\text{—}$
wherein z is 1 to about 15, or
a bond when s is a positive integer,
V is $\text{—}C(O)OR^3$ and $R^3$ is H, $CH_3$ or $R_f$;
$R^2$ is $C_1$ to $C_4$ alkyl, and
$M^+$ is a Group 1 metal or an ammonium $(NH_xR^2_y)^+$ cation wherein x+y=4, and $R^2$ is $C_1$ to $C_4$ alkyl,
provided that when Q is $\text{—}OP(O)(O^-M^+)(O)\text{—}$ or when Q is $\text{—}(CH_2CH_2O)_z\text{—}C(O)CH(SO_3^-M^+)CH_2C(O)(OCH_2CH_2)_z\text{—}$, then at least one of s or e is a positive integer.

The present invention further comprises a method of lowering surface tension of a medium comprising contacting the medium with a composition of Formula 1 as described above.

DETAILED DESCRIPTION

Trademarks are shown herein in upper case.

Herein the term "twin-tailed surfactant" is used to describe a surfactant having two hydrophobic groups attached to a connecting hydrophilic group. The two hydrophobic groups can be the same, denoted herein as "symmetrical twin-tailed surfactant". Alternatively the two hydrophobic groups can be dissimilar, denoted herein as "hybrid twin-tailed surfactant".

The present invention comprises hybrid twin-tailed surfactants having a lower fluorine content but which retain superior performance effects. It has been found in the present invention that when hydrocarbon (or alkylsilyl)hydrophobes are tethered to a fluorocarbon hydrophobe (oleophobe), surface tension values and critical micelle concentration values are approximately the same as for fully fluorinated surfactants.

The present invention comprises hybrid fluoroalkyl/alkyl surfactants of Formula 1.

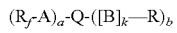   Formula 1 wherein
a and b are each independently 1 or 2;
$R_f$ is a linear or branched perfluoroalkyl radical having from 2 to about 20 carbon atoms, optionally interrupted with at least one oxygen;
R is a $C_1$ to $C_{20}$ linear, branched or cyclic alkyl, or a $C_6$ to $C_{10}$ aryl;
B is $\text{—}(CH_2CHR^1O)_x\text{—}$,
k is 0 or 1, x is 1 to about 20,
A is $\text{—}(CH_2)_m[(CHR^1CH_2O)]_s\text{—}[(CH_2)_m(CH)_t CHOH (CH_2)_m]_e\text{—}$,
wherein each m is independently 0 to 3, s is 0 to about 30, t is 0 or 1, and e is 0 or 1,
$R^1$ is H or $CH_3$,
Q is:
$\text{—}OP(O)(O^-M^+)(O)\text{—}$,
$\text{—}O\text{—}$,
$\text{—}S\text{—}(CH_2)_m\text{—}C(O)\text{—}O\text{—}$,
$\text{—}SO_2\text{—}O\text{—}$
$\text{—}CH_2CH_2O\text{—}C(O)CH_2C(OH)(V)CH_2C(O)O\text{—}$;
$\text{—}(CH_2CH_2O)_xCH_2CH(OH)(CH_2CH_2O)_x\text{—}(CH_2)_m\text{—}Si[OSi(R^2)_3]_2\text{—}$, $\text{—}SO_2NR^2\text{—}$,
$\text{—}(CH_2CH_2O)_zC(O)CH(SO_3^-M^+)CH_2C(O)(OCH_2CH_2)_z\text{—}$
wherein z is 1 to about 15, or a bond when s is a positive integer, V is —C(O)OR³ and R³ is H, CH₃ or $R_f$;

R² is $C_1$ to $C_4$ alkyl, and

M⁺ is a Group 1 metal or an ammonium $(NH_xR^2_y)^+$ cation wherein x+y=4, and R² is $C_1$ to $C_4$ alkyl, provided that when Q is —OP(O)(O⁻M⁺)(O)— or when Q is —(CH₂CH₂O)$_z$—C(O)CH(SO₃-M⁺)CH₂C(O)(OCH₂CH₂)$_z$—, then at least one of s or e is a positive integer.

Specific examples of the hybrid twin-tailed surfactants of Formula 1 include Formulae 2-9:

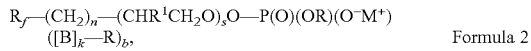
Formula 2

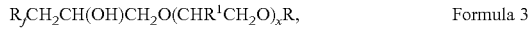
Formula 3

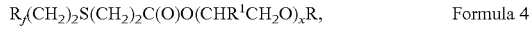
Formula 4

Formula 5

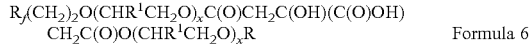
Formula 6

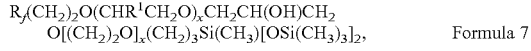
Formula 7

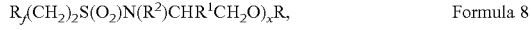
Formula 8 and

Formula 9

Where $R_f$, n, M⁺, R, R¹, B, k, b, x, and R2 are as defined above for Formula 1.

Specific examples of the above formulae appear in the Examples below.

The compositions of the present invention are surfactants for use in aqueous formulations, where extremely low surface tensions (about 18 dynes/cm=18 mN/m) are required. The surfactants of the present invention provide "fluorine efficiency". The term "fluorine efficiency" means to increase the efficiency or improve the performance of the surfactants so a lower proportion of the expensive fluorine component is required to achieve the same level of performance, or to have better performance using the same level of fluorine. The fluorine content of the surfactants of the present invention is about 50% or less compared with the fluorine content of conventional fluorinated surfactants.

While not wishing to be bound by theory, it is believed that physical mixtures of fluoroalkyl and hydrocarbon surfactants produce synergies in a number of applications. In such mixtures a "competition" exists, whereby the surface active materials vie for space at interfaces. It is believed that the more strongly hydrophobic fluoroalkyl groups preferentially displace the less strongly hydrophobic alkyl groups at the interface. However, when the fluoroalkyl and alkyl hydrophobic groups exist together in the same molecule, the alkyl hydrophilic groups cannot be displaced, and the surfactant properties are thereby improved. Furthermore, in the surfactants of the present invention, both the fluoroalkyl and alkyl groups have a high degree of freedom of movement, permitting unrestricted orientation at the interface. By contrast, Guo et al., in J. Phys. Chem., 1992, 10068-10074, vide supra, prepared fluoroalkyl/alkyl surfactants in which the fluoroalkyl group, the alkyl group, and the hydrophilic group were all bound to a single carbon atom. The tetrahedral structure for the carbon atom forces a separation in the orientation of the fluoroalkyl and alkyl groups (the bond angle is 109.5° for the H—C—H angle in the symmetrical tetrahedral methane molecule).

Most of Guo's examples did not show surface tension results as low as 18 mN/m. It is believed that the approximately 110° forced separation may diminish the effectiveness of the fluoroalkyl/alkyl combination in Guo's examples, compared with the structures of Formulae 2-9 above, wherein the hybrid fluoroalkyl and alkyl groups are unrestricted in orientation and can align themselves in the most favorable way. Additionally, compared with Guo's examples, the surfactants of the present invention are much easier to prepare, are obtained in higher yield, and provide improved hydrolytic stability.

The surfactants of the present invention can be conveniently prepared by a number of conventional means. For example, surfactants of Formula 2 are prepared by treating mixtures of fluoroalkyl and alkyl alcohols with phosphorous pentoxide, with subsequent hydrolysis and alkaline neutralization of the reaction mass. Further details are in U.S. Pat. No. 3,083,224. Alternatively, sequential reaction of fluoroalkyl and alkyl alcohols with phosphorous oxychloride (or, for example pyrophosphoryl chloride), followed by hydrolysis and neutralization can produce the desired materials.

Hybrid surfactants of the present invention of Formula 3 or 7 can be prepared in a one-step reaction from the Lewis-acid catalyzed condensation of a fluoroalkyl epoxide (such epoxide conveniently prepared as in U.S. Pat. Nos. 3,145,222 and 4,489,006) with a compound bearing an active hydrogen (e.g., an alcohol, alcohol alkoxylate, or amine). Catalysts include, but are not limited to, lanthanum group triflates or boron trifluoride etherate. The converse of this reaction works equally well; that is, the condensation reaction of a fluoroalkyl-substituted alcohol (or alkoxylate) with a hydrocarbon-, or alkyl silyl-substituted epoxide.

Hybrid surfactants of Formulas 4 or 6 are prepared by acid-catalyzed esterification of carboxylic acids with alcohols or alcohol alkoxylates. The reaction can utilize a fluorocarbon acid and hydrocarbon alcohol, or a hydrocarbon acid and a fluorocarbon alcohol. Further, the reaction is effected by the reaction of an alcohol with a carboxylic anhydride or acid chloride to give esters of the present invention. As above, it is possible to make surfactants of this type with fluoroalkyl acid derivatives (prepared, for example, as in U.S. Pat. No. 4,784,809 or 3,172,910) and hydrocarbon alcohols or with hydrocarbon acid derivatives and fluoroalkyl-substituted alcohols.

Hybrid surfactants of Formula 5 are readily prepared from the condensation reaction of a fluoroalkyl sulfonyl halide (prepared as in FR Patent 1600425) with a hydrocarbon alcohol or alcohol alkoxylate.

The present invention further comprises a method of lowering surface tension of a medium comprising contacting the medium with a composition of Formula 1 as described above. Any of a wide variety of media are suitable for use in the method of the present invention. Typically the medium is a liquid. Preferred are aqueous, hydrocarbon, and halocarbon systems. Examples of suitable medium include, for example, a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition of the present invention. The composition of the present invention is typically simply blended with or added to the medium. A low concentration of about 0.1% by weight of surfactant is sufficient to lower surface tension to less than about 24 mN/m, preferably less than about 22 mN/m, and most preferably less than about 20 mN/m. For many surfactants of the present invention concentrations of 0.01% by weight of the surfactant are effective to achieve a surface tension of less than about 22 mN/m.

The present invention further comprises a method of providing wetting and leveling to a coated substrate comprising adding to the coating base prior to deposition on the substrate, a composition comprising one or more compounds of formula (I) as described above. Suitable coating compositions, referred to herein by the term "coating base", include a composition, typically a liquid formulation, of an alkyd coating, Type I urethane coating, unsaturated polyester coating, or water-dispersed coating, and are described in *Outlines of Paint Technology* (Halstead Press, New York, N.Y., Third edition, 1990) and *Surface Coatings Vol. I, Raw Materials and Their Usage* (Chapman and Hall, New York, N.Y., Second Edition, 1984), herein incorporated by reference. Such coating bases are applied to a substrate for the purpose of creating a lasting film on the substrate surface. These are conventional paints, stains, floor polishes, and similar coating compositions.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as various classifications. Water-dispersed coatings in general contain other common coating ingredients. Water-dispersed coatings are exemplified by, but not limited to, pigmented coatings such as latex paints, unpigmented coatings such as wood sealers, stains, finishes, polishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Floor waxes, polishes, or finishes (hereinafter "floor finishes") are generally water based or solvent based polymer emulsions. The surfactants of Formula I of the present invention are suitable for use in such floor finishes. Commercially available floor finish compositions typically are aqueous emulsion-based polymer compositions comprising one or more organic solvents, plasticizers, coating aids, anti-foaming agents, surfactants, polymer emulsions, metal complexing agents, and waxes. The particle size range and solids content of the polymer are usually controlled to control the product viscosity, film hardness and resistance to deterioration. Polymers containing polar groups function to enhance solubility and may also act as wetting or leveling agents providing good optical properties such a high gloss and distinctness of reflected image.

Preferred polymers for use in floor finishes include acrylic polymers, polymers derived from cyclic ethers, and polymers derived from vinyl substituted aromatics. Acrylic polymers include various poly(alkyl acrylates), poly(alkyl methacrylates), hydroxyl substituted poly(alkyl acrylates) and poly (alkyl methacrylates). Commercially available acrylic copolymers used in floor finishes include, for example, methyl methacrylate/butyl acrylate/methacrylic acid (MMA/BA/MAA) copolymers; methyl methacrylate/butyl acrylate/acrylic acid (MMA/BA/AA) copolymers, and the like. Commercially available styrene-acrylic copolymers include styrene/methyl methacrylate/butyl acrylate/methacrylic acid (S/MMA/BA/MMA) copolymers; styrene/methyl methacrylate/butyl acrylate/acrylic acid (S/MMA/BA/A) copolymers; and the like. Polymers derived from cyclic ethers usually contain 2 to 5 carbon atoms in the ring with optional alkyl groups substituted thereon. Examples include various oxiranes, oxetanes, tetrahydrofurans, tetrahydropyrans, dioxanes, trioxanes, and caprolactone. Polymers derived from vinyl substituted aromatics include for example those made from styrenes, pyridines, conjugated dienes, and copolymers thereof. Polyesters, polyamides, polyurethanes and polysiloxanes are also used in floor finishes.

The waxes or mixtures of waxes that are used in floor finishes include waxes of a vegetable, animal, synthetic, and/or mineral origin. Representative waxes include, for example, carnuba, candelilla, lanolin, stearin, beeswax, oxidized polyethylene wax, polyethylene emulsions, polypropylene, copolymers of ethylene and acrylic esters, hydrogenerated coconut oil or soybean oil, and the mineral waxes such as paraffin or ceresin. The waxes typically range from 0 to about 15 weight percent and preferably from about 2 to about 10 weight percent based on the weight of the finish composition.

When used as additives to a coating base or floor finish the compositions of the present invention of Formula (I) as defined above are effectively introduced to the composition by thoroughly stirring it in at room or ambient temperature. More elaborate mixing can be employed such as using a mechanical shaker or providing heat or other methods. When used as an additive to coating bases or floor finishes, the compositions of the invention generally are added at about 0.001 weight % to about 5 weight % by dry weight of the composition of the invention in the wet composition. Preferably about from about 0.01 weight % to about 1 weight %, and more preferably from about 0.1 weight % to about 0.5 weight % is used.

The compounds of Formula I are useful in many additional applications due to their surfactant properties. The improved surfactant properties also provide improved foaming characteristics, reduced interfacial tension with hydrocarbon or halocarbon solvents, improved leveling of coatings, improved dynamic surface tension (the reduction of surface tension as a function of time).

Examples of some applications include the following.

The compounds represented by Formula I of the present invention are suitable for the use in fire fighting compositions, for example as a wetting agent, emulsifying agent and/or dispersant. They are also useful as a component in aqueous film forming extinguishing agents, and as an additive to dry chemical extinguishing agents in aerosol-type extinguishers, and as a wetting agent for sprinkler water.

The compounds of Formula I of the present invention are suitable for the use in agricultural compositions. Examples include as a wetting agent, emulsifying agent and/or dispersion agent for herbicides, fungicides, weed killers, parasiticides, insecticides, germicides, bactericides, nematocides, microbiocides, defoliants, fertilizers and hormone growth regulators. Formula I compounds are also suitable as a wetting agent for foliage, for live stock dips and to wet live stock skins; as an ingredient in sanitizing, discoloring and cleaning compositions; and in insect repellent compositions. The compounds of Formula 1 are also useful as a wetting agent, emulsifying agent and/or dispersion agent for the manufacture of paper and plywood veneer. The compounds of Formula I are also suitable for use as grease/oil repellents for paper, wood, leather, skins, metals, textiles, stone, and tiles, and as penetrant for preservative impregnation.

The compounds represented by Formula I of the present invention are also suitable for the use as a wetting agent, emulsifying agent and/or dispersion agent for polymerization reactions, particularly polymerization of fluoromonomers. These compounds are also suitable as a latex stabilizer; as an additive for foam applications to control spreading, crawling and edge buildup; as foaming agents, as mold release agents or as demolding agents; as an internal antistatic agent and antiblocking agent for polyolefins; as a flow modifier for extruding hot melts, spreading, uniformity, anticratering; and as a retarder for plasticizer migration or evaporation in the plastics and rubber industry.

The compounds of Formula I of the present invention are further suitable for the use in the petroleum industry as a wetting agent for oil well treatments, drilling mud; as a film evaporation inhibitor for gasoline, jet fuel, solvents, and hydrocarbons; as a lubricant or cutting oil improver to improve penetration times; as an oil spill collecting agent; and as additive to improve tertiary oil well recovery.

The compounds of Formula I of the present invention are further suitable for the use in textile and leather industries as a wetting agent, antifoaming agent, penetrating agent or emulsifying agent; or as a lubricant for textiles, nonwoven fabrics and leather treatment; for fiber finishes for spreading, and uniformity; as a wetting agent for dyeing; as a binder in nonwoven fabrics; and as a penetration additive for bleaches. The compounds of Formula I of the present invention are further suitable for the use in the mining and metal working industries, in the pharmaceutical industry, automotives, building maintenance and cleaning, in household, cosmetic and personal products, and in photography and The compounds of Formula 1 are useful as surfactants and leveling agents in aqueous solutions and emulsions. They are further useful to alter the surface properties of such media. The compositions of the present invention have enhanced fluorine efficiency compared to current commercial products. The inventive compositions provide the advantages of altering surface properties using less fluorine to achieve the same level of performance, or provide better performance using the same level of fluorine, as prior art compositions.

Test Methods and Materials

The following test methods and materials were used in the Examples herein.

Test Method 1—Wetting and Leveling Test

To test the performance of the samples in their wetting and leveling ability, the samples were added to a floor polish (RHOPLEX 3829, Formulation N-29-1, available from Rohm & Haas, Philadelphia, Pa.]) and applied to half of a thoroughly cleaned 12 inch×12 inch (30.36 cm×30.36 cm) vinyl tile (available from Interfuse Vinyl Tiles by Estrie, Sherbrooke, QC Canada). The tiles are thoroughly cleaned by wetting the tiles, adding a powdered oxygen bleach cleanser and scrubbing using a green SCOTCH-BRITE scouring pad, available from 3M Company, St. Paul Minn.). This scrubbing procedure was used to remove the pre-existing coating on the tiles. The tiles initially have a uniform shiny finish; a uniform dull finish indicates coating removal. The tiles are then air-dried overnight. A 1 wt % solution of the surfactant to be tested was prepared by dilution in deionized water. Following the resin manufacturer protocols, a 100 g portion of the RHOPLEX 3829 formulation was prepared, followed by addition of 0.75 g of the 1 wt % surfactant solution, to provide a test floor polish.

The test floor polish was applied to the tile by placing 3 mL portion of the test polish in the center of the tile, and spreading from top to bottom using a cheesecloth applicator, and finally placing a large "X" across the tile, using the applicator. The "X" subsequently provides visual evidence of leveling at the rating step. The applicator was prepared from a two-layer 18×36 inch (46×91 cm) sheet of cheesecloth (from VWR, West Chester Pa.), folded twice into an eight-layer pad. One corner of the pad was then used as the applicator. The tile was allowed to dry for 30 min. and a total of 5 coats (Coating #s 1-5) were applied and dried, with the X test performed after each coating had been dried. After each coat, the tile was rated on a 1 to 5 scale (1 being the worst, 5 the best) on the surfactant's ability to promote wetting and leveling of the polish on the tile surface. The rating is determined using the Tile Rating Scale below, based on comparison of a tile treated with the floor polish that contains no added surfactant

| Tile Rating Scale | |
|---|---|
| Score | Description |
| 1 | Uneven surface coverage of the film, significant streaking and surface defects |
| 2 | Numerous surface defects and streaks are evident but, generally, film coats entire tile surface |
| 3 | Visible streaking and surface defects, withdrawal of the film from the edges of the tile |
| 4 | Minor surface imperfections or streaking |
| 5 | No visible surface defects or streaks |

Test Method 2—Surface Tension Measurement.

Surface tension was measured according to the American Society for Testing and Materials ASTM # D1331-56, using the Wilhelmy plate method on a KRUSS K11 tensiometer [KRUSS USA, Matthews, N.C.]. Results are in mN/m (N·m× $10^{-7}$) (dynes/cm). The tensiometer was used according to the manufacturer's recommendations.

Test Method 3—Interfacial Tension by Drop Shape.

Interfacial tensions were measured at the phase boundary with cyclohexane using the pendant drop method (KRUSS DSA-100 pendant drop method, DSA1 drop shape analysis software SW3203) on a KRUSS DSA-100 surface analysis system (available from KRUSS USA, Matthews, N.C.).

Test Method 4—Critical Micelle Concentration (CMC).

The critical micelle concentration was measured by plotting the surface tension of the surfactant/water mixture versus the concentration of the surfactant and determining the point at which the surfactant concentration no longer has any appreciable influence on the surface tension.

Test Method 5-Ross-Miles Foam Test Measurements

Foaming characteristics were determined using the American Society for Testing and Materials Test Method ASTM # D1173-53. Foam depth was measured in mm.

Test Method 6—Wickbold Torch Method (for Fluorine Analyses)

An efficient process for the quantitative mineralization of fluorinated compounds is the Wickbold torch combustion method. The method (described in detail in Angew. Chem. 66 (1954) 173) was demonstrated to be compound independent for fluorine-containing compounds. In this process, the analytical sample was placed in a ceramic vessel and the sample, typically, was completely combusted by external heating in a vigorous oxygen stream. The gaseous reaction products wee passed through an auxiliary hydrogen/oxygen flame with excess oxygen, so the combustion became complete. The gaseous effluent was then condensed, and fluoride was solubilized in the aqueous stream which was collected for analysis. The aqueous fluoride was then easily measured, typically using a fluoride ion selective electrode.

Test Method 7—Blocking Resistance of Architectural Latex Paints

The test method described herein is a modification of ASTM D4946-89, Standard Test Method for Blocking Resistance of Architectural Paints, which is hereby specifically incorporated by reference. The face-to-face blocking resistance of paints to be tested was evaluated in this test. Blocking, for the purpose of this test, is defined as the undesirable sticking together of two painted surfaces when pressed together or placed in contact with each other for an extended period of time.

The paint to be tested was cast on a polyester test panel using an applicator blade. All painted panels were protected from surface contamination, such as grease, oil, fingerprints, dust, and the like. Typically, results were sought at 24 hours after casting the paint. After the panels had been conditioned in a conditioned room with controlled temperature and humidity as specified in the ASTM test method for the desired period of time, six squares (3.8 cm×3.8 cm) were cut out from the painted test panel. The cut sections (three pairs) were placed with the paint surfaces face-to-face for each of the paints to be tested. The face-to-face specimens were placed in a 50° C. oven on a marble tray. A no. 8 stopper was placed on top, with the smaller diameter in contact with the specimens, and then a 1000 g weight was placed on top of the stopper. This resulted in a pressure of 1.8 psi (12,400 Pascal) on the specimens. One weight and stopper was used for each specimen tested. After exactly 30 minutes, the stoppers and weights were taken off the test specimens which were removed from the oven and allowed to cool in the conditioned room for 30 minutes before determining the resistance to blocking.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in the Table entitled Blocking Resistance Numerical Ratings below. The degree of seal was estimated from the appearance of the specimens and the fraction of the paint surfaces that adhere. Paint tearing away from the test panel backing was an indication of seal. A higher number indicated better resistance to blocking.

| Blocking Resistance Numerical Ratings | | |
| --- | --- | --- |
| Blocking Resistance Numerical Ratings | Description of the Separation | Performance Description |
| 10 | No tack | Perfect |
| 9 | Trace tack | Excellent |
| 8 | Very slight tack | Very good |
| 7 | Slight tack | Good/very good |
| 6 | Moderate to slight tack | Good |
| 5 | Moderate tack | Fair |
| 4 | Very tacky, no seal | Poor to Fair |
| 3 | 5-25% seal | Poor |
| 2 | 25-50% seal | Poor |
| 1 | 50-75% seal | Very poor |
| 0 | 75-100% seal | Very poor |

Materials

The following materials were used in the Examples herein.

1) A mixture of $C_8$-$C_{14}$ perfluoroalkylethanols [$F(CF_2CF_2)_n(CH_2CH_2)OH$] where n is 3 to 6, is available from E.I. du Pont de Nemours and Company, Wilmington Del. Alcohols of this composition are referred to herein as "telomer B alcohol".

2) TERGITOL 15-S-series (15-S-n, $R(OCH_2CH_2)_nOH$), is commercially available from Dow Chemical, Midland Mich.

3) RHOPLEX 3829, formulation N-29-1 floor polish is available from Rohm & Haas, Philadelphia, Pa.

4) VISTA 6400 paints having an acrylic semi-gloss resin with 84% gloss at 85 degrees is available from Vista Paints, Fullerton, Calif.

EXAMPLES

Example 1

Telomer B alcohol [$F(CF_2)_n(CH_2CH_2)OH$, n=average 7, 70.6 g, 0.17 mol, 75 mole %], 1-octanol [$C_8H_{17}OH$, 7.4 g, 0.057 mol, 25 mole %] and phosphoric anhydride [$P_2O_5$ 14.2 g, 0.10 mol, mole %] were reacted. The mixture was neutralized with a slight excess of 5% aqueous ammonia to pH 8.5, and dissolved in a mixture of water [44.6 g, 2.5 mol] and 2-propanol [$(CH_3)_2CHOH$, 93.9 g, 1.6 mol] yielding a solution of the ammonium salts of perfluoroalkylethyl-octyl phosphate esters (Formula 2). Surface tension was measured by Test Method 2 and is shown in Table 1.

Examples 2-4

Solutions of the ammonium salts of perfluoroalkylethyl-octyl phosphate esters were prepared as in Example 1 using, for Example 2, 50 mole % telomer B alcohol and 50 mole % 1-octanol; for Example 3, 25 mole % telomer B alcohol and 75 mole % 1-octanol (Ex. 3); and, for Example 4, 12.5 mole % telomer B alcohol and 87.5 mole % 1-octanol. Surface tension was measured by Test Method 2 of these mixed phosphates in deionized water at various weight %, and is shown in Table 1.

Comparative Example A

Comparative Example A was prepared as in Example 1 using 100 mole % telomer B alcohol and no 1-octanol. Surface tension measurements by Test Method 2 for Comparative Example A in deionized water at various weight % as shown in Table 1.

TABLE 1

Surface Tension Measurements

| Ex. # | Telomer:1-Octanol Ratio | Surfactant Concentration in Distilled Water (wt %) | | | | | | | | |
|---|---|---|---|---|---|---|---|---|---|---|
| | | 0 | 0.001 | 0.005 | 0.01 | 0.05 | 0.10 | 0.50 | 1.00 | 5.00 |
| | | Surface Tension by Test Method 2 (mN/m) | | | | | | | | |
| Comp A | 100:0 | 67.4 | 47.4 | 36.1 | 27.8 | 25.0 | 23.6 | 19.7 | 19.5 | 19.5 |
| 1 | 75:25 | 67.8 | 40.5 | 35.1 | 33.2 | 25.3 | 21.4 | 20.8 | 20.2 | 17.1 |
| 2 | 50:50 | 70.5 | 30.8 | 21.7 | 20.2 | 17.9 | 16.6 | 16.6 | 16.4 | 16.4 |
| 3 | 25:75 | 69.5 | 33.3 | 30.3 | 22.6 | 20.5 | 19.2 | 17.5 | 17.5 | 17.1 |
| 4 | 12.5:87.5 | 71.3 | 45.3 | 33.0 | 27.0 | 21.4 | 20.0 | 17.6 | 17.6 | 17.7 |

Table 1 shows that all the Examples (mixed perfluoroalkylethyl/octyl phosphate esters) showed a lower surface tension compared to the Comparative Example A (the perfluoroalkylethyl ester without octyl ester groups). Example 2 with 50:50 mole ratio of the perfluoroalkylethyl/octyl phosphate ester has the lowest surface tension. Even Example 4 with the lowest fluoroalcohol content (12.5 mole %) had a surface tension less than Comparative Example A, which contains by weight the three perfluoroalkyl phosphate ammonium salts 1:1:1), 3-7%; (1:1:2), 17-21%; and (2:1:1), 11-15% for an overall 75 mole % fluoroalcohol.

Example 5

The synthesis of hybrid sulfoethoxylates (Formula 5) was effected by a two-step preparation of the perfluorohexylethyl sulfonyl chloride followed by a condensation reaction with TERGITOL 15-S-series (15-S-n, $R(OCH_2CH_2)_nOH$), commercially available from Dow Chemical, Midland Mich. The number associated with "n" in the TERGITOL 15-S-series product name and structure is the average number of ethylene oxide chains on the secondary alcohol ethoxylate.

Perfluorohexylethyl iodide [$C_6F_{13}CH_2CH_2I$, bp 138-210° C., 301 g, 0.63 mol], acetic acid [$CH_3COOH$, bp 118° C., 3.4 g, 0.06 mol], ethanol [$CH_2CH_2OH$, bp 78° C., 112 g, 2.44 mol] and potassium thiocyanate [KSCN, bp 500° C., 75.7 g, 0.78 mol] were refluxed at 80° C. with magnetic stirring for 12 hours when the remaining unreacted iodide was under 0.5%, as confirmed by GC analysis. The mixture was cooled to 60° C. and solids were removed by a medium fritted glass filter funnel aided by slight vacuum of 15 in Hg (50.7 kPa). The warm solid filter cake was washed with 100 g. of warm (60° C.) ethanol. The ethanol solvent was distilled from the filtrate and the perfluorohexylethyl thiocyanate product was washed with warm (55° C.) deionized water. The perfluorohexylethyl thiocyanate product was a yellow-orange solid at room temperature ($C_6F_{13}CH_2CH_2SCN$, 230 g, yield 90%).

Gas chromatographic analysis (performed using an Agilent Technologies 6850 gas chromatograph equipped with FID and employing a capillary column [HP-1 (30 m×0.32 mm)] over a temperature range of 50-300° C. (8° C. min$^{-1}$)) showed that the thiocyanate [retention time 4.305 min.] was 99% pure. $^1$H NMR (500 MHz; MeOD) δ 2.70-2.80 (m, 2H), δ 4.45-4.50 (m, 2H).

The perfluorohexylethyl thiocyanate [$C_6F_{13}CH_2CH_2SCN$, bp<300° C., 224 g, 0.55 mol] prepared as above and acetic acid [$CH_3COOH$, bp 118° C., 116 g, 1.94 mol] were heated with an oil bath to 45° C. and agitated with a mechanical stirrer. Chlorine [bp −34° C., 130 g, 1.85 mol] was bubbled into the reaction at a rate of 0.002 moles/min. of chlorine per mole of perfluorohexylethyl thiocyanate and de-ionized water [44 g, 2.47 mol] was simultaneously added drop wise at a rate of 0.004 moles/min of de-ionized water per mole of thiocyanate reagent over a 10 h period by an automatic syringe. This oxidation reaction was run until the concentration of perfluorohexylethyl thiocyanate starting material was below 0.5% as determined by GC analysis. The product was washed with 100 ml of 70° C. de-ionized water and then 100 mL of 60° C. 3.5% NaCl solution. The perfluorohexylethyl sulfonyl chloride product ($C_6F_{13}CH_2CH_2SO_2Cl$, 242 g, yield 99%) was a yellow liquid. Gas Chromatographic analysis showed that the perfluorohexylethyl sulfonyl chloride (retention time 4.542 min.) was 99% pure. $^1$H NMR (500 MHz; $CH_3OD$) δ 2.70-2.80 (m, 2H), δ 4.45-4.50 (m, 2H).

The perfluorohexylethyl sulfonyl chloride [$C_6F_{13}CH_2CH_2SO_2Cl$, bp>200° C., 10 g, 0.02 mol] prepared as above and TERGITOL 15-S-12 [$C_{13}H_{27}(OCH_2CH_2)_{12}OH$, bp>200° C., 17.8 g, 0.02 mol] were heated with an oil bath and agitated with a magnetic spin bar. A nitrogen sweep was bubbled at the liquid surface. When the temperature of the reaction reached 75° C., the reaction became homogenous and clear. The temperature was held at 80° C. for 7 hours. The product was a clear, yellow-brown liquid ($C_6F_{13}CH_2CH_2SO_2(OCH_2CH_2)_{12}OC_{13}H_{27}$, 25.5 g, yield 100%). $^1$H NMR (500 MHz; $CDCl_3$) δ 0.80 (5, 2H), δ 1.00-1.05 (d, 2H), δ 1.20 (m, 2H), δ 1.30-1.40 (m, 2H), δ 2.90-3.00 (m, 2H), δ 3.45-3.50 (t, 3H), δ 3.50-3.60 (m, 2H), δ 3.70-3.80 (m, 2H), δ 4.45-4.50 (m, 2H).

Example 6

The synthesis of hybrid ethoxylates of formulae 3 were formed by a Lewis acid-catalyzed reaction of the perfluorohexyl propylene oxide and alcohol ethoxylates typified by TERGITOL® 15-S-series surfactants (e.g., 15-S-n, $R(OCH_2CH_2)_nOH$).

Perfluorohexyl iodide [$C_6F_{13}I$, bp 117° C., 1500 g, 3.36 mol] and tris allyl borate [$B(OCH_2CHCH_2)_3$, 171° C., 306 g, 1.68 mol] were heated with an oil bath to 64° C. with moderate agitation with a magnetic stirrer and nitrogen sweep. The temperature of the reaction was kept between 60-70° C. VAZO 64 (propanenitrile, 2-methyl, 2,2'-azobis, $NCC(CH_3)_2NNC(CH_3)_2CN$, mp 102° C., 11 g, 0.07 mol, available from E.I. du Pont de Nemours and Company, Wilmington Del.) was added in 2 g increments every 3 hours. An exotherm was observed after the first and second VAZO 64 additions. There was no exothermic reaction after a total of 10 g of VAZO 64 had been added to the reaction. Warm 60° C. de-ionized water [$H_2O$, 750 g, 41.6 mol] and salt [NaCl, 35 g, 0.6 mol] was added to hydrolyze borate esters. The reaction was then heated to carry out an azeotropic distillation to remove volatile organics (mostly allyl alcohol). The reaction was cooled and the aqueous and organic layers were separated. After cooling, the iodohydrin product ($C_6F_{13}CH_2CH(I)CH_2OH$, 1500 g, yield 99%) was a white solid. Gas chromatographic analyses performed using an Agilent Technologies 6850 gas chromatograph equipped with FID and employing a capillary column [HP-1 (30 m×0.32 mm)] over a temperature range of 50-300° C. (8° C. min$^{-1}$). GC analysis showed that the perfluorohexyl iodohydrin [retention time 8.932 min.] was 98.5% pure. $^1$H NMR (500 MHz; CDCl$_3$) δ 2.6-2.8 (m, 2H), δ 2.8-3.0 (m, H), δ 3.7-3.8 (m, 2H), δ 4.2-4.4 (m, H).

The perfluorohexyl iodohydrin [$C_6F_{13}CH_2CH(I)CH_2OH$, bp>200C, 750 g, 1.5 mol] prepared above and anhydrous methanol [$CH_3OH$, bp 65° C., 150 g, 0.19 mol] were agitated by a mechanical stirrer and cooled to below 5° C. Potassium hydroxide [KOH, 91 g, 1.09 mol] was diluted to 50% (w/w) with deionized water, and added to the reaction dropwise over a period of 3 hours keeping the reaction temperature below 6° C. The reaction was continued (monitored by GC analysis) until the concentration of the starting iodohydrin was below 0.5%. The reaction was warmed to room temperature then neutralized with a 10% bisulfate solution [NaHSO$_4$, 400 g, 2.94 mol]. The perfluorohexyl propylene oxide product ($C_6F_{13}CH_2CHOCH_2$, bp 154° C.) was distilled under vacuum. The product (456 g, yield 81%) collected was a clear colorless liquid. GC analysis showed that the perfluorohexyl propylene oxide (retention time 3.352 min.) was 92.4% pure. $^1$H NMR (500 MHz; CDCl$_3$) δ 2.2-2.5 (m, 2H), δ 2.6-2.7 (m, H), δ 2.8-2.9 (m, 2H).

Perfluorohexyl propylene oxide [$C_6F_{13}CH_2CHOCH_2$, bp 154° C., 25 g, 0.07 mol] prepared as above, TERGITOL® 15-S-12 [R(OCH$_2$CH$_2$)$_{12}$OH, bp>200° C., 50.8 g, 0.07 mol], and boron trifluoride etherate [BF$_3$(C$_2$F$_5$)O, bp 125° C., 0.15 g, 1.06 mmol] were warmed to 90° C. with an oil bath and agitated with a magnetic stir bar in a dry nitrogen atmosphere over a one-hour period. When the temperature reached 85° C., the reaction became homogenous and clear. The temperature was held at 90° C. for 4 hours. The condensation product was a clear, orange liquid with a small amount of sediment at the bottom ($C_6F_{13}CH_2CHOHCH_2(OCH_2CH_2)_{12}OC_{13}H_{27}$, 77 g, yield 100%). GC analysis showed that the hybrid ethoxylate (retention time 7.101 min.) was 78.0% pure. $^1$H NMR (500 MHz; CDCl$_3$) δ 0.80 (5, 2H), δ 1.00-1.05 (d, 2H), δ 1.20 (m, 2H), δ 1.30-1.40 (m, 2H), δ 2.15-2.25 (m, H), δ 2.30-2.40 (m, 2H), δ 3.40-3.50 (m, 3H), δ 3.55-3.65 (m, 2H), δ 3.70-3.80 (m, 2H), δ 4.05-4.15 (m, 2H).

Comparative Example B

Comparative Example B was a fluoroethoxylate (R$_f$CH$_2$CH$_2$(CH$_2$CH$_2$O)$_n$H, n is about 7), which is prepared by the reaction of telomer B alcohol with ethylene oxide. A glass flask was equipped with an agitator and dry ice condenser, a subsurface gas inlet tube, and in inert nitrogen atmosphere at ambient pressure. Fluorinated alcohol, (244 g, approximately 0.55 mole) of F(CF$_2$)$_m$CH$_2$CH$_2$OH, having the following approximate distribution: 4% of m is 2 to 4, 35% of m is 6, 30% of m is 8, 17% of m is 10, 8% of m is 12, and 6% of m is 14 or greater, was charged to the flask and then dehydrated by heating to 80C under a sparge of inert gas. Sodium borohydride (1.02 g, 0.027 mole) and iodine (1.8 g, 0.007 mole) were added, and the mixture stirred and heated to 140-145C. Charging of the ethylene oxide was initiated by bubbling the gas into the reaction subsurface through the gas inlet tube, the rate of addition maintained so that a slow reflux of the ethylene oxide was observed in the condenser. The resulting fluoroalkyl ethoxylate product had an average of about 7 ethylene oxide units per molecule. Surface Tension measurements were made by Test Method 2. The critical micelle concentration (CMC) was measured according to Test Method 4. Results are shown in Table 2.

TABLE 2

Critical Micelle Concentrations (CMC) and Surface Tension Measurements versus Surfactant Concentration

| | | % Fluorine of Surfactant in Deionized Water | | | |
|---|---|---|---|---|---|
| Example | CMC Value | 0.0001% | 0.001% | 0.01% | 0.10% |
| | | Surface Tension by Test Method 2 (mN/m) | | | |
| Comparative Example B | 0.01% | 48.12 | 22.14 | 18.27 | 18 |
| 5 | 0.01% | 56.34 | 37.76 | 26.25 | 23.67 |
| 6 | 0.05% | 54.72 | 22.39 | 20.83 | 20.61 |

Table 2 shows that Examples 5 and 6, with both a perfluoroalkyl group and a hydrocarbon group present, had similar critical micelle concentrations compared to the Comparative Example B (the perfluoroalkylethyl ethoxylate). That is, the surfactants of the present invention are effective at reducing surface tension at very low concentrations, even when compared to fully-fluorinated surfactants.

The hybrid surfactants of Example 6 were used to reduce interfacial tension and dynamic interfacial tension (i.e., interfacial tension as a function of time) between water and hydrocarbon solvents (e.g., cyclohexane). This phenomenon is useful in improving coatings, creating emulsions, and in fire-fighting applications. Interfacial Tension Measurements (mN/m) of Example 6 and Comparative Example B were carried out at 0.01% concentration in deionized water. Interfacial tensions were measured at the phase boundary with cyclohexane using Test Method 3. Results are in Table 3

TABLE 3

Interfacial Tension Measurements versus Time

| | Interfacial Surface Tension (mN/m) as a Function of Surface Age of 0.01% Concentration of Surfactant in Deionized Water | | | | |
|---|---|---|---|---|---|
| Example | 20 s | 40 s | 60 s | 80 s | 100 s |
| De-ionized Water - No Surfactant | 49.57 | 49.35 | 48.57 | 47.68 | 47.47 |
| Comparative Example B | 19.08 | 17.79 | 16.92 | 16.42 | 16.11 |
| Example 6 | 18.50 | 16.21 | 14.99 | 14.29 | 13.74 |

Table 3 shows that Example 6 consistently had a lower interfacial tension with cyclohexane than the Comparative Example B. Interfacial tension at phase boundaries between water and halogenated liquids was reduced using Example 6. This is particularly useful in creating emulsions of halogenated materials in aqueous media for the purpose of conducting polymerization, e.g. of tetrafluoroethylene.

Interfacial Tension (mN/m) was measured of hybrid twin-tail surfactant Example 6 at 0.01% concentration in deionized water at the phase boundary with CF$_3$CHFCHFCF$_2$CF$_3$, available from E.I. du Pont de Nemours and Company, Wilmington Del.). Interfacial tension was measured according to Test Method 3. The results are in Table 4.

TABLE 4

Interfacial Tension Measurements versus Time

| | Interfacial tension (mN/m) as a function of surface age of 0.01% w/w Surfactant in Deionized Water at the VERTREL XF phase boundary. | | | | |
|---|---|---|---|---|---|
| Example | 20 s | 40 s | 60 s | 80 s | 100 s |
| No Surfactant | 39.56 | 38.75 | 38.36 | 38.15 | 37.93 |
| Comparative Example B | 26.2 | 25.15 | 24.67 | 24.23 | 23.95 |
| Example 6 | 20.56 | 19.38 | 18.79 | 18.14 | 17.47 |

Table 4 shows that fluorocarbon/hydrocarbon hybrid (Example 6) lowered the interfacial tension consistently better than fully-fluorinated Comparative Example B.

The foaming propensities of hybrid surfactants Examples 5 and 6 and Comparative Example B at 0.1% active ingredient with deionized water were measured by Test Method 5. Results are in Table 5.

TABLE 5

Foam Height Measurements

| | Foam Height | | |
|---|---|---|---|
| Example | Initial (mm) | 5 min. (mm) | 10 min. (mm) |
| Example 5 | 135 | 45 | 14 |
| Example 6 | 6 | 1 | 1 |
| Comparative Example B | 22 | 18 | 17 |

The data in Table 5 shows that a fluorocarbon/hydrocarbon hybrid ethoxylate of Example 6 had lower foaming properties than the fully fluorinated Comparative Example B, making it useful, for example, in coatings applications where foam is an undesired attribute. The fluorocarbon/hydrocarbon hybrid ethoxylate of Example 5 had greater foaming properties than the fully fluorinated Comparative Example B, making it useful for example in creating foam "blankets" in fire-fighting applications.

Comparative Example B and Example 6 were added to RHOPLEX 3829, formulation N-29-1, floor polish, available from Rohm & Haas, Philadelphia, Pa., in an amount of 1.0% active ingredient and tested for wetting and leveling according to Test Method 1. The results are in Table 6.

TABLE 6

Sample Scores by Test Method 1

| Coating | Blank | Comparative Example B | Example 6 | Dry Time (minutes) |
|---|---|---|---|---|
| 1 | 3 | 3 | 3 | 40 |
| 2 | 2 | 4 | 3 | 40 |
| 3 | 1 | 4 | 3 | 30 |
| 4 | 1 | 4 | 3 | 30 |
| 5 | 1 | 4 | 3 | 30 |

Example 6, containing 50% of the fluorine content of Comparative Example B, was superior in leveling compared to the blank and had similar leveling performance compared to the fully fluorinated Comparative Example B. Thus, the surfactants of the present invention containing fluoroalkyl and hydrocarbon groups unexpectedly show excellent leveling at very low concentrations, even when compared to fully-fluorinated surfactants.

Comparative Example C and Example 7

Esterification of citric acid, using alcohol ethoxylates and fluoroalcohol ethoxylates was conducted to create mixed esters of Formula 6. Two separate 500-ml round bottom, 4-neck flasks, equipped with stirrers, condensers with Dean-Stark Traps, and heating mantles with thermostat controllers were charged with the reagents listed in Table 7.

TABLE 7

Amount of reagents

| Reagents (g): | Comparative Example C | Example 7 |
|---|---|---|
| Citric Acid | 10 | 10 |
| Perfluoroalkyl ethoxylate* | 76 | 38 |
| BRIJ 56** | 0 | 36.5 |
| Toluene | 90 | 90 |

(plus additional Toluene to pre-fill the Dean Stark Traps)
*Perfluoroalkyl ethoxylate ($R_fCH_2CH_2(CH_2CH_2O)_7H$, $R_{f\,average} = C_7F_{15}$), MW = ~730
**Uniqema BRIJ 56 ($C_{16}H_{33}(CH_2CH_2O)_{10}H$) = MW = 683

The reactors were heated to a gentle reflux under dry nitrogen. Boiling began at about 111°-112° C. Boiling temperature gradually increased to 115°-116° C. over the next 2 h, and small amount of water began to collect in the Dean-Stark traps. After about 3 h, about 1 mL water had been captured in each. The temperature was then reduced below the boiling point and 0.3 g p-toluenesulfonic acid monohydrate was added to each reactor. Heating was resumed and the contents were refluxed overnight.

The traps were then inspected; Comparative Example C had about 1.4 mL of water, Example 7 had about 1.9 mL of water, and each had about 20 mL of toluene. Reflux was continued for another 8 h, during which time the traps were drained 4 more times. Next, the toluene was distilled off, giving about 65 mL of additional toluene from each vessel. The vessels were then allowed to cool overnight.

Sodium bicarbonate (10 mL of a solution of 0.34 g in 25 mL water) was added at room temperature to each vessel with agitation. Foaming was minor. Both of the products were added to separate 500-ml one-neck round-bottom flasks and the toluene stripped off the products in a rotary evaporator. Foaming was controlled by the addition of 15 g of 2-propanol to each flask. Additional aliquots of 50% water/2-propanol were added and stripping of the toluene continued until there was no remaining odor of toluene. The products obtained were as follows:

Comparative Example C: $HOC(CH_2CO_2X)_2CO_2X$, $X=(CH_2CH_2O)_7CH_2CH_2R_f$ $R_f$ average=$C_7F_{15}$ Example 7 (Mixed Ester):
12.5% $HOC(CH_2CO_2X)_2CO_2X$,
12.5% $HOC(CH_2CO_2Y)_2CO_2Y$
25% $HOC(CH_2CO_2X)(CH_2CO_2Y)CO_2X$
25% $HOC(CH_2CO_2X)(CH_2CO_2Y)CO_2Y$ where
$X=(CH_2CH_2O)_7CH_2CH_2R_f$ and
$Y=(CH_2CH_2O)_{10}(CH_2)_{15}CH_3$ ($R_{f\,average}=C_7F_{15}$)

The surface tension of Comparative Example C and Example 7 were measured according to Test Method 2. The results are in Table 8.

TABLE 8

Surface tension versus concentration

| Example | % Concentration of Surfactant in Deionized Water | | | |
|---|---|---|---|---|
| | 0.001% | 0.01% | 0.10% | 1.00% |
| | Surface Tension by Test Method 2 (mN/m) | | | |
| Comparative Example C | 59 | 30 | 26 | 23 |
| Example 7 | 54 | 30 | 24 | 21 |

The hybrid surfactant of Example 7 had equivalent performance compared to a Comparative Example C, prepared with twice as much of the fluorinated ethoxylate. Thus Example 7 demonstrated comparable performance at 50% of the fluorine content, providing an increase in fluorine efficiency.

Example 8

A 250 mL three-neck flask equipped with mechanical stirrer assembly, a thermocouple, and reflux condenser connected to a nitrogen line was charged with $R_fCH_2CH_2(CH_2CH_2O)_7H$, [$R_{f\ average}$=$C_7F_{15}$, 150.0 g, 205 mmol] followed by powdered potassium hydroxide [KOH, 90%, 18.4 g, 329 mmol]. The addition of the caustic caused a slight exotherm and a darkening of the resulting suspension. The mixture was stirred for 10 min., cooled to 0° C., and epichlorohydrin [$CH_2OCHCH_2Cl$, 27.5 mL, 350 mmol] was added dropwise. Upon complete addition the reaction mixture was allowed warm to ambient temperature and further stirred at 55° C. for 12 h. Diethyl ether (200 mL) was added to the reaction mixture and the suspension filtered. The solids were washed with diethyl ether (50 mL). The collected filtrates were thoroughly dried under reduced pressure (200 mbar), initially at ambient temperature and finally at 70° C. The perfluoroalkyl propylene oxide product of Formula 7 was a viscous amber oil ($R_fCH_2CH_2Q(CH_2CH_2O)_nCH_2CHOCH_2$, $R_{f\ average}$=$C_7F_{15}$, Q=O, $n_{average}$=8, 178 g, 98%). $^1$H NMR (CDCl$_3$) δ 2.31 (m, 2H, $CF_2CH_2$), 2.49 (m, 1H, $CH_2CH(O)CH_2$), 2.67 (m, 1H, $CH_2CH(O)CH_2$), 3.05 (m, 1H, $CH_2CH(O)CH_2$), 3.32 (m, 1H, $CH_2CH(O)CH_2$), 3.05 (m, 1H, $CH_2CH(O)CH_2$), 3.40-3.65 (m, 32H, $OCH_2$), 3.68 (m, 3H, $CH_2CH(O)CH_2$ and $CF_2CH_2CH_2O$).

A 250-mL three-neck flask equipped with mechanical stirrer assembly, a thermocouple, and reflux condenser connected to a nitrogen line was charged with the perfluoroalkyl propylene oxide [$R_fCH_2CH_2Q(CH_2CH_2O)_nCH_2CHOCH_2$, 138.5 g, 176 mmol] prepared as above and Dow Q2-5211 [$HO(CH_2CH_2O)_mCH_2CH_2CH_2Si(CH_3)_3O[Si(CH_3)]_xOSi(CH_3)_3$, 109 g, 176 mmol]. Boron trifluoride etherate [$BF_3(C_2F_5)O$, 2.5 g, 18 mmol] was added and the reaction mixture stirred at 50° C. for 5 h. Amberlyst A-21 (18 mmol) and methanol (CH$_3$OH, 50 mL) is added. After 30 min. of stirring the mixture was filtered. All volatiles were removed under reduced pressure (200 mbar). The heptamethyl trisiloxane addition product was an amber oil of Formula 7, $R_fCH_2CH_2Q(CH_2CH_2O)_nCH_2CHOHCH_2O(CH_2CH_2O)_mCH_2CH_2CH_2R^2$ $^1$H NMR (CDCl$_3$) □ -0.08 (s, 3H, SiCH$_3$), -0.01 (s, 18H, SiCH$_3$), 0.35 (m, 2H, SiCH$_2$), 0.85 (m, 1H), 1.53 (m, 3H, SiCH$_2$CH$_2$), 2.33 (m, 2H, SiCH$_2$CH$_2$), 3.32 (m, 2H, SiC$_3$H$_9$OCH$_2$), 3.40-3.65 (m, 32H, OCH$_2$), 3.68 (m, 3H, $CH_2CH(O)CH_2$ and $CF_2CH_2CH_2O$).

The surface tension of Example 8 and Comparative Example B were measured using Test Method 2. The results are in Table 9.

TABLE 9

Surface Tension versus Concentration

| Example | % Concentration of Surfactant in Deionized Water | | | |
|---|---|---|---|---|
| | 0.001% | 0.01% | 0.10% | 1.00% |
| | Surface Tension by Test Method 2 (mN/m) | | | |
| Comparative Example B | 22 | 18 | 18 | 17 |
| Example 8 | 54 | 30 | 24 | 21 |

The data in Table 9 shows that Example 8, containing 50% less fluorine than Comparative Example B, has performance comparable to Comparative Example B at concentrations of about 0.10% or higher.

Example 9

In a round bottom flask equipped with a thermocouple and a magnetic stirrer bar, POCl$_3$ (1.3 g, 8.6 mmoles) was dissolved in 25 mL of dry tetrahydrofuran. The solution was cooled to 0° C. using an ice-bath. A separate solution containing fluorinated alcohol, $C_6F_{13}CH_2CH_2OH$ (3.1 g, 8.6 mmoles) and triethylamine (2.1 g, 21 mmoles) in 15 mL of dry tetrahydrofuran was slowly added to the reactor. The reaction was allowed to proceed for 1-2 hours at 0° C. Then, a solution of the hydrocarbon alcohol, 1-octanol (1.1 g, 8.6 mmoles), in 15 mL of dry tetrahydrofuran was slowly added to the reaction mass. The reaction was stirred overnight at ambient temperature. Then, the solids were filtered and the solvent evaporated using the rotovap. The resulting oil was diluted in 10 mL of tetrahydrofuran and 0.34 g (8.6 mmol) of NaOH dissolved in 1 mL of water was added to the reaction mass. The mixture was stirred overnight at room temperature. Then, the solvent was evaporated using the rotovap, the resulting solids were washed with 50 mL of chloroform, and filtered. The final product was dried at 120° C. and 150 mmHg (20 kPa) inside a vacuum oven. The product was a compound of Formula 1 wherein $R_f$ is $C_6F_{13}$, A is $CH_2CH_2$ (s and e are each 0 and m is 2), Q is OP(O)(O$^-$M$^+$)(O), M is Na, k is 0, R is $C_8H_{17}$, and b is 1. Surface tension was measured using Test Method 2 and the results are in Table 11.

Examples 10-16

The process of Example 9 was employed using different hydrocarbon alcohols in the amounts as listed in Table 10. The products were compounds of Formula 1 wherein $R_f$ is $C_6F_{13}$, A is $CH_2CH_2$ (s and e are each 0 and m is 2), Q is OP(O)(O$^-$M$^+$)(O), M is Na, k is O, b is 1, and for Example 10 R is $C_8H_{17}$, for Example 11 R is $C_4H_9$, for Example 12 R is $C_5H_{11}$, for Example 13 R is $C_7H_{15}$, for Example 14 R is $C_9H_{19}$, for Example 15 R is $C_{10}H_{21}$ and for Example 16 R is $(CH_2)_2C_6H_{13}$. Surface tension was measured using Test Method 2 and the results are in Table 11.

Examples 17-20

The process of Example 9 was employed with the following variations. In Example 17 the fluorinated alcohol and 1-octanol were mixed together and added in a single step. In Example 18 the 1-octanol was added first and the fluorinated alcohol in a second step. In Examples 19 and 20 differing amounts of the fluorinated alcohols and i-octanol as shown in Table 10 were employed. The products obtained were the same as in Example 9. Surface tension was measured using Test Method 2 and the results are in Table 11.

Comparative Example D

The process of Example 9 was employed except that twice the amount of fluorinated alcohol was reacted and no hydrocarbon alcohol was used. The product obtained was similar to Formula 1 but contained a second $R_f$ group in place of R, so that each $R_f$ is $C_6F_{13}$, A is $CH_2CH_2$ (s and e are each 0 and m is 2), Q is $OP(O)(O^-M^+)(O)$, M is Na, k is 0, and b is 1.

Comparative Example E

The process of Example 9 was employed except that twice the amount of the hydrocarbon alcohol, 1-octanol, was reacted and no fluorinated alcohol was used. The product obtained was similar to Formula 1 but contained a second R group in place of $R_f$, so that each R is $C_8H_{17}$, A is $CH_2CH_2$ (s and e are each 0 and m is 2), Q is $OP(O)(O^-M^+)(O)$, M is Na, k is 0, and b is 1.

TABLE 11-continued

| | Surface Tension | | | |
|---|---|---|---|---|
| Example | % Fluorine | 0.5* | 0.1* | 0.05* | 0.01* |
| 19 | 16.8 ± 1.5 | 16.6 ± 0.1 | 16.4 ± 0.3 | 17.3 ± 0.1 | 28.9 ± 1.9 |
| 20 | 35.7 ± 1.9 | 17.9 ± 0.1 | 21.4 ± 0.8 | 24.1 ± 0.9 | 24.0 ± 0.9 |

*Concentration of surfactant in solution, weight %

Table 11 shows the surface tension results for Examples 9-20 and Comparative Examples D and E. The average results and standard deviations were obtained from the individual testing of three different solutions of surfactants. The fluorine content of each surfactant as specified in Table 11 is for the dried surfactants and was determined by Test Method 6. In general all the Examples 9-20 demonstrated similar or superior performance to the Comparative Example D while having lower fluorine content at concentrations of 0.5, 0.1 and 0.05 weight % in solution. Several of the Examples demonstrated superior performance at a concentration of 0.01% by weight in solution. The performance of Examples 9, 16, 17, 18 and 19 as each required only 0.05% by weight in solution to reduce the surface tension of water below 20 dynes/cm. (mN/m).

TABLE 10

| Example | Phosphorous oxychloride Amount, g | mmol | Triethylamine Amount, g | mmol | Fluorinated alcohol Name | Amount, g | mmol | Hydrocarbon alcohol Name | Amount, g | Mmol | Average % Yield |
|---|---|---|---|---|---|---|---|---|---|---|---|
| Comparative D | 1.3 | 8.6 | 2.1 | 21 | C6* | 6.3 | 17 | n/a | 0 | 0 | 82 |
| 9 | 1.3 | 8.6 | 2.1 | 21 | C6 | 3.1 | 8.6 | 1-octanol | 1.1 | 8.6 | 75 |
| 10 | 1.3 | 8.6 | 2.1 | 21 | C6 | 3.1 | 8.6 | 1-hexanol | 0.88 | 8.6 | 75 |
| 11 | 1.3 | 8.6 | 2.1 | 21 | C6 | 3.1 | 8.6 | 1-butanol | 0.64 | 8.6 | 83 |
| 12 | 1.3 | 8.6 | 2.1 | 21 | C6 | 3.1 | 8.6 | 1-pentanol | 0.76 | 8.6 | 69 |
| 13 | 1.3 | 8.6 | 2.1 | 21 | C6 | 3.1 | 8.6 | 1-heptanol | 1.0 | 8.6 | 79 |
| 14 | 1.3 | 8.6 | 2.1 | 21 | C6 | 3.1 | 8.6 | 1-nonanol | 1.2 | 8.6 | 72 |
| 15 | 1.3 | 8.6 | 2.1 | 21 | C6 | 3.1 | 8.6 | 1-decanol | 1.4 | 8.6 | 76 |
| 16 | 1.3 | 8.6 | 2.1 | 21 | C6 | 3.1 | 8.6 | 2-ethylhexanol | 1.1 | 8.6 | 63 |
| Comparative E | 1.3 | 8.6 | 2.1 | 21 | n/a | 0 | 0 | 1-octanol | 2.3 | 17 | 25 |
| 17 | 1.3 | 8.6 | 2.1 | 21 | C6 | 3.1 | 8.6 | 1-octanol | 1.1 | 8.6 | 67 |
| 18 | 1.3 | 8.6 | 2.1 | 21 | C6 | 3.1 | 8.6 | 1-octanol | 1.1 | 8.6 | 67 |
| 19 | 1.3 | 8.6 | 2.1 | 21 | C6 | 1.6 | 4.3 | 1-octanol | 1.7 | 13 | 49 |
| 20 | 1.3 | 8.6 | 2.1 | 21 | C6 | 4.7 | 13 | 1-octanol | 0.60 | 4.3 | 70 |

*C6 indicates the fluorinated alcohol $C_6H_{13}CH_2CH_2OH$ for Examples 9-20 and Comparative Example D

TABLE 11

| | Surface Tension | | | |
|---|---|---|---|---|
| Example | % Fluorine | 0.5* | 0.1* | 0.05* | 0.01* |
| Comparative D | 50.3 ± 3.8 | 20.9 ± 1.8 | 24.6 ± 1.0 | 24.8 ± 0.4 | 25.3 ± 0.9 |
| Comparative E | 0.0 | 22.5 ± 0.2 | 31.8 ± 1.2 | 36.2 ± 1.3 | 36.9 ± 2.0 |
| 11 | 34.8 ± 3.3 | 16.5 ± 2.1 | 24.2 ± 6.8 | 29.9 ± 8.9 | 38.7 ± 2.3 |
| 12 | 35.1 ± 6.6 | 15.9 ± 0.1 | 21.2 ± 3.1 | 27.4 ± 5.2 | 36.0 ± 2.8 |
| 10 | 34.2 ± 2.9 | 16.2 ± 0.8 | 18.9 ± 1.3 | 24.2 ± 3.0 | 36.1 ± 3.7 |
| 13 | 32.1 ± 1.4 | 16.5 ± 1.0 | 17.4 ± 1.1 | 21.6 ± 1.9 | 30.9 ± 2.8 |
| 9 | 37.1 ± 6.7 | 17.8 ± 0.0 | 18.4 ± 0.1 | 19.7 ± 0.5 | 29.2 ± 1.8 |
| 14 | 30.9 ± 0.9 | 19.5 ± 1.0 | 20.6 ± 0.6 | 22.0 ± 1.0 | 29.5 ± 2.6 |
| 15 | 30.1 ± 2.3 | 19.9 ± 1.3 | 21.6 ± 0.7 | 22.5 ± 0.8 | 27.5 ± 2.6 |
| 16 | 34.0 ± 2.6 | 15.9 ± 0.7 | 17.7 ± 1.1 | 20.9 ± 1.8 | 24.5 ± 1.0 |
| 17 | 26.7 ± 1.6 | 16.5 ± 0.4 | 17.9 ± 0.7 | 19.4 ± 0.6 | 26.8 ± 1.7 |
| 18 | 22.8 ± 1.9 | 16.1 ± 0.5 | 17.4 ± 1.1 | 19.3 ± 1.9 | 28.4 ± 2.2 |

Examples 21-27

The process of Example 9 was employed except the fluorinated alcohol was $C_4F_9CH_2CH_2OH$ in the amount shown in Table 12, and the hydrocarbon alcohol was as indicated in the amounts shown in Table 12. The products were compounds of Formula 1 wherein $R_f$ is $C_4F_9$, A is $CH_2CH_2$ (s and e are each 0 and m is 2), Q is $OP(O)(O^-M^+)(O)$, M is Na, k is 0, b is 1, and for Example 21 R is $C_4H_9$, for Example 22 R is $C_5H_{11}$, for Example 23 R is $C_6H_{13}$, for Example 24 R is $C_7H_{15}$, for Example 25 R is $C_8H_{17}$, for Example 26 R is $C_9H_{19}$ and for Example 27 R is $C_{10}H_{21}$. Surface tension was measured using Test Method 2 and the results are in Table 13.

Comparative Example F

The process of Example 9 was employed except that twice the amount of fluorinated alcohol was reacted and no hydrocarbon alcohol was used. The product obtained was similar to Formula 1 but contained a second $R_f$ group in place of R, so that each $R_f$ is $C_4F_9$, A is $CH_2CH_2$ (s and e are each 0 and m is 2), Q is $OP(O)(O^-M^+)(O)$, M is Na, k is 0, and b is 1.

tested for blocking in accordance with Test Method 7. The resulting data is shown in Tables 14 and 15.

TABLE 12

| Example | Phosphorous oxychloride Amount, g | mmol | Triethylamine Amount, g | mmol | Fluorinated alcohol Name | Amount, g | mmol | Hydrocarbon alcohol Name | Amount, g | Mmol | Average % Yield |
|---|---|---|---|---|---|---|---|---|---|---|---|
| 21 | 0.58 | 3.8 | 1.0 | 9.5 | C4 TBA | 1.0 | 3.8 | 1-butanol | 0.28 | 3.8 | 85 |
| 22 | 0.58 | 3.8 | 1.0 | 9.5 | C4 TBA | 1.0 | 3.8 | 1-pentanol | 0.33 | 3.8 | 82 |
| 23 | 0.58 | 3.8 | 1.0 | 9.5 | C4 TBA | 1.0 | 3.8 | 1-hexanol | 0.39 | 3.8 | 87 |
| 24 | 0.58 | 3.8 | 1.0 | 9.5 | C4 TBA | 1.0 | 3.8 | 1-heptanol | 0.44 | 3.8 | 93 |
| 25 | 0.58 | 3.8 | 1.0 | 9.5 | C4 TBA | 1.0 | 3.8 | 1-octanol | 0.49 | 3.8 | 97 |
| 26 | 0.58 | 3.8 | 1.0 | 9.5 | C4 TBA | 1.0 | 3.8 | 1-nonanol | 0.55 | 3.8 | 70 |
| 27 | 0.58 | 3.8 | 1.0 | 9.5 | C4 TBA | 1.0 | 3.8 | 1-decanol | 0.60 | 3.8 | 95 |
| Comparative F | 0.58 | 3.8 | 1.0 | 9.5 | C4 TBA | 2.0 | 7.6 | n/a | 0.00 | 0 | |

TABLE 13

Surface Tension

| Example | % Fluorine | Concentration, % wt. | | | | | | |
|---|---|---|---|---|---|---|---|---|
| | | 0.5 | 0.1 | 0.05 | 0.01 | 0.005 | 0.0025 | 0.001 |
| Comparative F | 55.9 | 14.6 | 22.2 | 27.3 | 33.8 | 39.0 | 43.6 | 50.6 |
| 21 | 42.7 | 17.5 | 32.4 | 37.4 | 48.2 | 53.8 | 60.8 | 68.2 |
| 22 | 41.3 | 17.2 | 33.1 | 39.6 | 48.6 | 54.6 | 59.8 | 63.9 |
| 23 | 39.9 | 16.6 | 28.4 | 35.6 | 46.4 | 50 | 55.3 | 62.3 |
| 24 | 38.7 | 16.2 | 26.5 | 29.9 | 40.3 | 45.8 | 49.8 | 57.3 |
| 25 | 37.5 | 17.3 | 23.3 | 28.5 | 36.3 | 40.2 | 46.8 | 50 |
| 26 | 36.4 | 17.5 | 17.9 | 21.7 | 29.4 | 32.3 | 39.2 | 46.7 |
| 27 | 35.3 | 18.3 | 19.3 | 21.4 | 30.2 | 33.6 | 34.6 | 43.4 |

Table 13 shows the surface tension results for the Examples 21-27 hybrid phosphates. The hybrid surfactants were compared against the non-hybrid Comparative Example F. The fluorine content of each surfactant was calculated from the amount of reagents used for the synthesis as specified on Table 13. In general Examples 21-27 demonstrated similar performance to the Comparative Example F while having lower fluorine content. Examples 25-27 generally demonstrated superior performance. Examples 21-24, which each contained a shorter chain hydrocarbon group R, were less effective than Examples 25-27, which each contained a longer chain hydrocarbon group R, indicating that as the fluorine is decreased, a longer hydrocarbon tail is desirable. The most significant improvement in fluorine efficiency was observed for Examples 26 and 27. These two surfactants were capable of reducing the surface tension of water below 20 dynes/cm (mN/m) while using much less fluorine than Comparative Example F.

Testing in Paint

A 5% by weight aqueous dispersion of Examples 15, 18, and Comparative Example D were prepared. Each of these was added to 100 g of VISTA 6400 paint in the amount listed in Table 14 to provide 70 ppm (micrograms/g) of fluorine. Each of these were also added to 100 g of VISTA 6400 paint in the amount of 0.28 g to provide a fluorine content as listed in Table 15. The paint was applied to polyester test panels and

TABLE 14

Blocking scores at same fluorine content

| Example | Paint | Weight dose | Fluorine dose | Average blocking score |
|---|---|---|---|---|
| Comparative Example D | Vista 6400 | 0.28 g | 70 ppm | 5.0 |
| Example 18 | Vista 6400 | 0.61 g | 70 ppm | 5.3 |
| Example 15 | Vista 6400 | 0.46 g | 70 ppm | 8.0 |

Table 14 compares the blocking performance of Comparative Example D against Examples 15 and 18 at same fluorine content. The test was carried out following Test Method 7 in which the test samples are rated from 0 to 10. Higher blocking scores represent better blocking performance. Both Examples 15 and 18 demonstrated superior performance than Comparative Example D. These two examples also enhance fluorine efficiency as demonstrated by their higher blocking scores at the same level of fluorine concentration.

TABLE 15

Blocking scores at same weight content

| Example | Paint | Weight dose | Fluorine dose | Average blocking score |
|---|---|---|---|---|
| Comparative Example D | Vista 6400 | 0.28 g | 70 ppm | 5.0 |
| Example 18 | Vista 6400 | 0.28 g | 32 ppm | 6.0 |
| Example 15 | Vista 6400 | 0.28 g | 42 ppm | 7.0 |

Table 15 compares the blocking performance of Comparative Example D against Examples 15 and 18 at same weight content. The test was carried out following Test Method 7 in which the test samples are rated from 0 to 10. Higher blocking scores represent better blocking performance. Both Examples 15 and 18 demonstrated superior performances at significantly lower fluorine content than Comparative Example D. These results are consistent with enhanced fluorine efficiency provided by the hybrid nature of the Examples.

What is claimed is:

1. A surfactant of formula 1

$$(R_f\text{-}A)_a\text{-}Q\text{-}([B]_k\text{---}R)_b \qquad \text{Formula 1}$$

wherein
a and b are each independently 1 or 2;
$R_f$ is a linear or branched perfluoroalkyl radical having from 2 to about 20 carbon atoms, optionally interrupted with at least one oxygen;
R is a $C_1$ to $C_{20}$ linear, branched or cyclic alkyl, or a $C_6$ to $C_{10}$ aryl;
B is —$(CH_2CHR^1O)_x$—,
k is 0 or 1, x is 1 to 20,
A is $(CH_2)_m[(CHR^1CH_2O)]_s$—$[(CH_2)_m(CH)_tCHOH(CH_2)_m]_e$—,
wherein
each m is independently 0 to 3, s is 0 to 30, t is 0 or 1, and e is 0 or 1,
$R^1$ is H or $CH_3$,
Q is:
—S—$(CH_2)_m$—C(O)—O—,
—$SO_2$—O—
—$CH_2CH_2O$—C(O)$CH_2$C(OH)(V)$CH_2$C(O)O—;
$(CH_2CH_2O)_xCH_2CH(OH)$—$CH_2O$—$(CH_2CH_2O)_x$—$(CH_2)_m$—$Si[OSi(R^2)_3]^2$—,
—$SO_2NR^2$—,
—$(CH_2CH_2O)_zC(O)CH(SO_3^-M^+)CH_2C(O)(OCH_2CH_2)_z$— wherein z is 1 to 15, or
a bond when s is a positive integer,
V is —C(O)$OR^3$ and $R^3$ is H, $CH_3$ or $R_f$;
$R^2$ is $C_1$ to $C_4$ alkyl, and
$M^+$ is a Group 1 metal or an ammonium $(NH_xR^2_y)^+$ cation wherein x and y are each independently 0 to 4, and x+y=4, and $R^2$ is $C_1$ to $C_4$ alkyl,
provided that when Q is —$(CH_2CH_2O)_z$—C(O)CH$(SO_3^-M^+)CH_2C(O)(OCH_2CH_2)_z$—, then at least one of s or e is a positive integer.

2. The surfactant of claim 1 having the following formula $$R_f(CH_2)_2S(CH_2)_2C(O)O(CHR^1CH_2O)_xR$$

wherein
$R_f$, $R^1$, x and R are as defined in claim 1.

3. The surfactant of claim 1 having the following formula $$R_f(CH_2)_2S(O_2)O(CHR^1CH_2O)_xR$$

wherein
$R_f$, $R^1$, x and R are as defined in claim 1.

4. The surfactant of claim 1 having the following formula $$R_f(CH_2)_2O(CHR^1CH_2O)_xC(O)CH_2C(OH)(C(O)OH)CH_2C(O)O(CHR^1CH_2O)_xR$$

wherein
$R_f$, $R^1$, x and R are as defined in claim 1.

5. The surfactant of claim 1 wherein A is —$(CH_2)_m[(CHR^1CH_2O)]_s$—$[(CH_2)_m(CH)_tCHOH(CH_2)_m]_e$— wherein m is 0, s is 2, e is 0, and $R^1$ is as defined in claim 1; a is 1; Q is —$(CH_2CH_2O)_xCH_2$—CH(OH)$CH_2O$—$(CH_2CH_2O)_x$—$(CH_2)_m$Si$[OSi(R^2)_3]_2$— wherein x, m, and $R^2$ are as defined in claim 1; k is 0; b is 1; and $R_f$ and R are as defined in claim 1.

6. The surfactant of claim 1 having the following formula $$R_f(CH_2)_2S(O_2)N(R^2)(CHR^1CH_2O)_xR$$

wherein
$R_f$, $R^1$, $R^2$, x and R are as defined in claim 1.

7. The surfactant of claim 1 wherein Q is —$(CH_2CH_2O)_zC(O)CH(SO_3^-M^+)CH_2C(O)(OCH_2CH_2)_z$—, wherein z is 1 to 15, and $R_f$, A, a, B, k, R, and b are as defined in claim 1.

8. The surfactant of claim 1 having a surface tension of less than about 25 mN/in at a concentration of 0.1% by weight in water.

9. The surfactant of claim 1 having a surface tension of less than about 20 mN/in at a concentration of 0.5% by weight in water.

* * * * *